United States Patent

Sezginer

Patent Number: 6,107,797
Date of Patent: Aug. 22, 2000

[54] MAGNETIC RESONANCE LOGGING APPARATUS AND METHOD

[75] Inventor: Abdurrahman Sezginer, Houston, Tex.

[73] Assignee: Schlumberger Technology Corporation, Ridgefield, Conn.

[21] Appl. No.: 09/198,715

[22] Filed: Nov. 24, 1998

Related U.S. Application Data

[63] Continuation-in-part of application No. 08/936,892, Sep. 25, 1997, abandoned.
[51] Int. Cl.$^7$ .......................................................... G01V 3/00
[52] U.S. Cl. ............................................. 324/303; 324/318
[58] Field of Search ........................................ 324/303, 300, 324/312, 314, 307, 309, 318, 322

[56] References Cited

U.S. PATENT DOCUMENTS

| | | |
|---|---|---|
| 4,035,718 | 7/1977 | Chandler . |
| 4,528,508 | 7/1985 | Vail, III . |
| 4,656,422 | 4/1987 | Vail, III et al. . |
| 4,710,713 | 12/1987 | Strikman ................................. 324/303 |
| 4,717,878 | 1/1988 | Taicher et al. . |
| 4,724,385 | 2/1988 | Vail, III ................................... 324/303 |
| 4,804,918 | 2/1989 | Vail, III ................................... 324/303 |
| 5,055,787 | 10/1991 | Kleinberg et al. ....................... 324/303 |
| 5,055,788 | 10/1991 | Kleinberg et al. ....................... 324/303 |
| 5,332,967 | 7/1994 | Shporer .................................. 324/303 |
| 5,363,041 | 11/1994 | Sezginer ................................. 324/303 |
| 5,428,291 | 6/1995 | Thomann et al. . |
| 5,596,274 | 1/1997 | Sezginer ................................. 324/303 |
| 5,914,598 | 6/1999 | Sezginer et al. ........................ 324/303 |
| 5,977,768 | 11/1999 | Sezginer et al. ........................ 324/303 |

FOREIGN PATENT DOCUMENTS

| | | |
|---|---|---|
| PCT/EP96/ 0291 | 6/1996 | WIPO . |
| PCT/US96/ 15301 | 9/1996 | WIPO . |

OTHER PUBLICATIONS

S. Connolly, G. Glover, D. Nishimura, and A. Macovski, MRM 18, 28, 1991.
Webb, Rev. Sci. Inst., V48, p. 1585, 1978.
Ernst et al., "Principles Of Nuclear Magnetic Resonance In One And Two Dimensions", pp. 91–241, Clarendon Press, 1987.
S. Connolly, D. Nishimura, A. Macovski JMR 83, pp. 324–334, 1989.
M. Garwood and Y. Ke, J. Mag. Res., 94, pp. 511–525, 1991.
T. Hwang, P. Van Zijl and M. Garwood, JMR 124, pp. 250–254, 1997.
R. de Graaf, K. Nicolay, M. Garwood, MRM, 35, pp. 652–657, 1996.
A. Abragam, The Principles Of Nuclear Magnetism, Oxford Univ. Press, 1961 pp. 65–68, 86, Fig. III 5 and III 6.
P. Mansfield, Pulsed Magnetic Resonance, pp. 317–345, 1992.

(List continued on next page.)

*Primary Examiner*—Louis Arana
*Attorney, Agent, or Firm*—William B. Batzer; Martin M. Novack

[57] ABSTRACT

A logging device for measuring nuclear magnetic resonance characteristics of earth formations surrounding a borehole having means for producing a static magnetic field in formations surrounding the borehole, means for producing an audio frequency magnetic field in the formations, means for rotating the static magnetic field with respect to the audio frequency magnetic field, and means for detecting nuclear magnetic resonance signals from spins in the formation precessing around the earth's magnetic field. A method of measuring nuclear magnetic resonance characteristics of earth formations surrounding a borehole using such a device is also described. In its preferred form, the invention involves an NMR technique and apparatus in which spins in the formations are tipped by adiabatic fast passage, resulting in a relatively large depth of investigation, but does not require treating of the borehole fluid.

26 Claims, 4 Drawing Sheets

OTHER PUBLICATIONS

S.C. Bushong, ScD, "Magnetic Resonance Imaging Physical and Biological Principles", Houston, Texas, pp. 279–297.

Bagguley, D.M.S., "Pulsed Magnetic Resonance: NMR, ESR, And Optics A Recognition Of E.L. Hahn", 1992, pp. 317–345.

Melton and Pollak, JMRA 122, pp. 42–49, 1996.

Solomon, Phys. Rev. Lett. 2, pp. 301–302, 1952.

E.J. Wells And K.H. Abramson, JMR, 1, pp. 378–392, 1969.

Hwang, VanZijil and Garwood, JMR, 133, pp. 200–203, 1998.

Garwood and Ugurbill, "$B_1$ Insensitive Adiabatic RF Pulses" in "NMR Basic Principles and Progress", M. Ruin and J. Seelig, Eds., pp. 109–144, Springer–Verlag, N.Y., 1992.

A. Tannus and M. Garwood, JMR A 120, pp. 133–137, 1996.

E. Kupce and R. Freeman JMR A 118, pp. 299–303, 1996.

T.L. Hwang and A.J. Shaka, JMR A 112, pp. 275–279, 1995.

M.H. Levitt and R. Freeman JMR 43, pp. 65–80, 1981.

V. Ermakov, J. Bohlen, G. Bodenhausen, JMR A 103, pp. 226–229 1993.

O.A. Trushkin, O.A. Shushnakov, & A.V. Legchenko, "Surface NMR Applied to an Electronconductive Medium", Geophysical Prospecting, 1995, 43, 623–633.

O.A. Shushnakov, "Surface NMR Measurement of Proton Relaxation Times in Medium to Coarse–Grained Sand Aquifier", 1996, Magnetic Resonance Imaging, vol. 14, Nos. 7/8 pp. 959–960.

R.C. Merrick, S.H. Coutruie, & D.L. Best, "An Improved Nuclear Magnetism Logging System and Its Application to Formation Evaluation", Sep. 23–26, 1979, Las Vagas, Nevada, SPE 8361.

MAGNETIC RESONANCE LOGGING APPARATUS AND METHOD

RELATED APPLICATIONS

This is a continuation-in-part of U.S. patent application Ser. No. 08/936,892, filed Sep. 25, 1997 now abandoned, and assigned to the same assignee as the present Application. The subject matter of present Application is related generally to the subject matter of U.S. patent application Ser. No. 09/198,535 [60.1344] and the subject matter of U.S. patent application Ser. No. 09/199,019 [60.1302], both filed of even date herewith, and both assigned to the same assignee as the present Application.

FIELD OF THE INVENTION

This invention relates to nuclear magnetic resonance logging, and, more particularly, to a method and apparatus for magnetic resonance logging of an earth borehole to obtain information about properties of formations surrounding the earth borehole.

BACKGROUND OF THE INVENTION

General background of nuclear magnetic resonance (NMR) well logging is set forth, for example, in U.S. Pat. No. 5,023,551. Briefly, in conventional NMR operation the spins of nuclei align themselves along an externally applied static magnetic field. This equilibrium situation can be disturbed by a pulse of an oscillating magnetic field (e.g. an RF pulse), which tips the spins away from the static field direction. After tipping, two things occur simultaneously. First, the spins precess around the static field at the Larmor frequency, given by $\omega_0 = \gamma B_0$, where $B_0$ is the strength of the static field and $\gamma$ is the gyromagnetic ratio. Second, the spins return to the equilibrium direction according to a decay time T1, the spin lattice relaxation time. For hydrogen nuclei, $\gamma/2\pi = 4258$ Hz/Gauss, so, for example, for a static field of 235 Gauss, the frequency of precession would be 1 MHz. Also associated with the spin of molecular nuclei is a second relaxation, T2, called the spin-spin relaxation time. At the end of a ninety degree tipping pulse, all the spins are pointed in a common direction perpendicular to the static field, and they all precess at the Larmor frequency. The net precessing magnetization decays with a time constant T2 because the individual spins rotate at different rates and lose their common phase. At the molecular level, dephasing is caused by random motions of the spins. The magnetic fields of neighboring spins and nearby paramagnetic centers appear as randomly fluctuating magnetic fields to the spins in random motion. In an inhomogeneous field, spins at different locations precess at different rates. Therefore, in addition to the molecular spin—spin relaxation of fluids, spatial inhomogeneities of the applied field also cause dephasing. Spatial inhomogeneities in the field can be due to microscopic inhomogeneities in the magnetic susceptibility of rock grains or due to the macroscopic features of the magnet.

A widely used technique for acquiring NMR data both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then a one hundred eighty degree pulse is applied to cause the spins which are dephasing in the transverse plane to reverse direction and to refocus. By repeatedly reversing the spins using one hundred eighty degree pulses, a series of "spin echoes" appear, and the train of echoes is measured and processed.

Further background, set forth in the referenced copending parent application Ser. No. 08/936,892, is summarized as follows: The static field may be naturally generated, as is the case for the earth's magnetic field $B_E$. The NML™ nuclear logging tool of Schlumberger measures the free precession of proton nuclear magnetic moments in the earth's magnetic field. See, for example, U.S. Pat. No. 4,035,718. The tool has at least one multi-turn coil wound on a core of non-magnetic material. The coil is coupled to the electronic circuitry of the tool and cooperatively arranged for periodically applying a strong DC polarizing magnetic field, $B_P$, to the formation in order to align proton spins approximately perpendicular to the earth's field, $B_E$. The characteristic time constant for the exponential buildup of this spin polarization is the spin-lattice relaxation time, $T_1$. At the end of polarization, the field is rapidly terminated. Since the spins are unable to follow this sudden change, they are left aligned perpendicular to $B_E$ and therefore precess about the earth's field at the Larmor frequency $f_L = \gamma B_E$. The Larmor frequency in the earth's field varies from approximately 1300 to 2600 Hz, depending on location. The spin precession induces in the coil a sinusoidal signal of frequency $f_L$ whose amplitude is proportional to the number of protons present in the formation. The tool determines the volume of free fluid in the formation. Additives in the borehole fluid are required to prevent the borehole fluid signal from dominating the formation signal. Also, there is necessarily a significant wait time before transients die down so that the coil can be used for detecting relatively small magnetic resonance signals.

A further nuclear magnetic resonance approach employs a locally generated static magnetic field, $B_o$, which may be produced by one or more permanent magnets, and RF antennas to excite and detect nuclear magnetic resonance (using, for example, the type of RF pulse sequence first described above), to determine porosity, free fluid ratio, and permeability of a formation. See, for example, U.S. Pat. Nos. 4,717,878 and 5,055,787.

As pointed out in the referenced copending Application, the tools and techniques developed in the prior art have various drawbacks that limit their utility in practical applications. These limitations include, among others, one or more of the following: a shallow depth of investigation, difficulty in obtaining interpretable results in washed out formations or where certain types of invasion have occurred, restrictions on the shape and size of the region of investigation, the need for treating of the borehole fluid, and the need for significant waiting between transmission and receiving.

It is among the objects of the present invention to address limitations of prior art nuclear magnetic resonance logging techniques and apparatus, and to devise improved logging methods and equipment for obtaining magnetic resonance characteristics of earth formations surrounding a borehole.

SUMMARY OF THE INVENTION

The present invention is directed, in its preferred form, to an NMR technique and apparatus in which spins in the formations are tipped by adiabatic fast passage. The technique, which results in a relatively large depth of investigation, utilizes the geomagnetic field, but does not require treating of the borehole fluid.

In accordance with an embodiment of the apparatus of the invention, there is provided an apparatus for measuring a nuclear magnetic resonance characteristic of earth formations surrounding a borehole. A logging device is movable through the borehole. Means are provided in the logging device for producing a static magnetic field in formations surrounding the borehole and for producing an audio frequency magnetic field in the formations. Means are also provided in the logging device for rotating the static magnetic field with respect to the audio frequency magnetic field. Nuclear magnetic resonance signals, from spins in the formations precessing around earth's magnetic field, are detected at the logging device.

In a preferred embodiment of the invention, the means for rotating the static magnetic field with respect to the audio frequency magnetic field comprises means for mechanically rotating the static magnetic field producing means.

Also in the preferred embodiment, the means for producing a static field comprises a permanent magnet. The permanent magnet is elongated in the direction of the longitudinal axis of the logging device, and the magnet is polarized in a direction transverse the direction of the longitudinal axis.

Also in the preferred embodiment, the means for producing the audio frequency magnetic field comprises a coil and means for applying an audio frequency energizing signal to the coil. The coil is wound on an axis that is perpendicular to the longitudinal axis of the logging device, and the coil is elongated in the direction of the longitudinal axis. The audio frequency is a frequency in the range between about 1 kHz to 3 kHz, which is the Larmor frequency of the geomagnetic field.

Further features and advantages of the invention will become more readily apparent from the following detailed description when taken in conjunction with the accompanying drawings.

BRIEF DESCRIPTION OF THE DRAWINGS

FIG. 4, which includes

DETAILED DESCRIPTION

Figure 1:
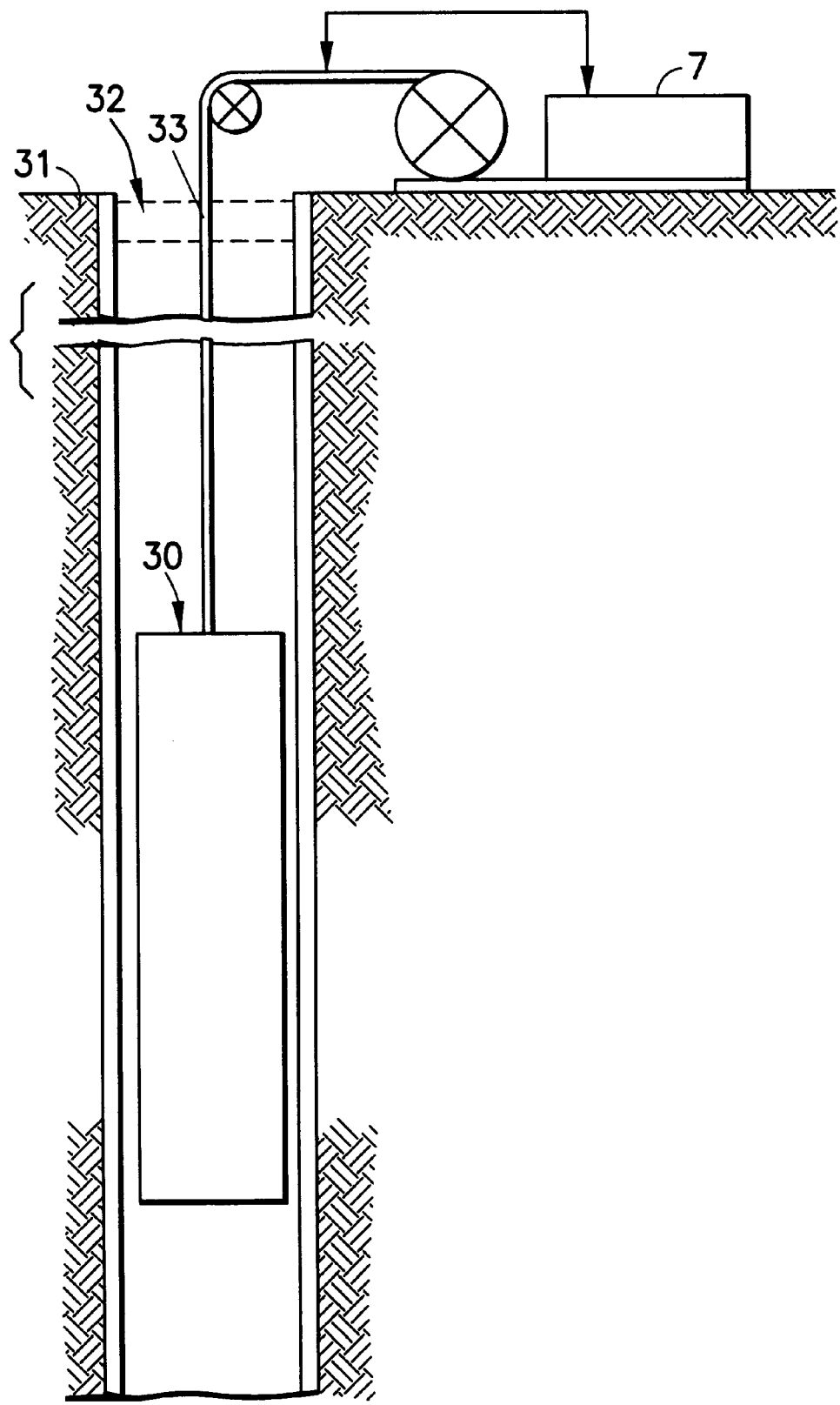
FIG. 1 is a diagram, partially in schematic and partially in block form, that can be used in practicing embodiments of the invention.

Referring to FIG. 1, there is shown an apparatus for investigating subsurface formations 31 traversed by a borehole 32, which can be used in practicing embodiments of the invention.

An investigating apparatus or logging device or tool 30 is suspended in the borehole 32 on an armored cable 33, the length of which substantially determines the relative depth of the device 30. The cable length is controlled by suitable means at the surface such as a drum and winch mechanism (not shown). Surface equipment, represented at 7, can be of conventional type, and can include a processor subsystem which communicates with the downhole equipment. Although a wireline embodiment is shown, it will be understood that variations of the invention could be used in a measurement while drilling system.

Figure 2:
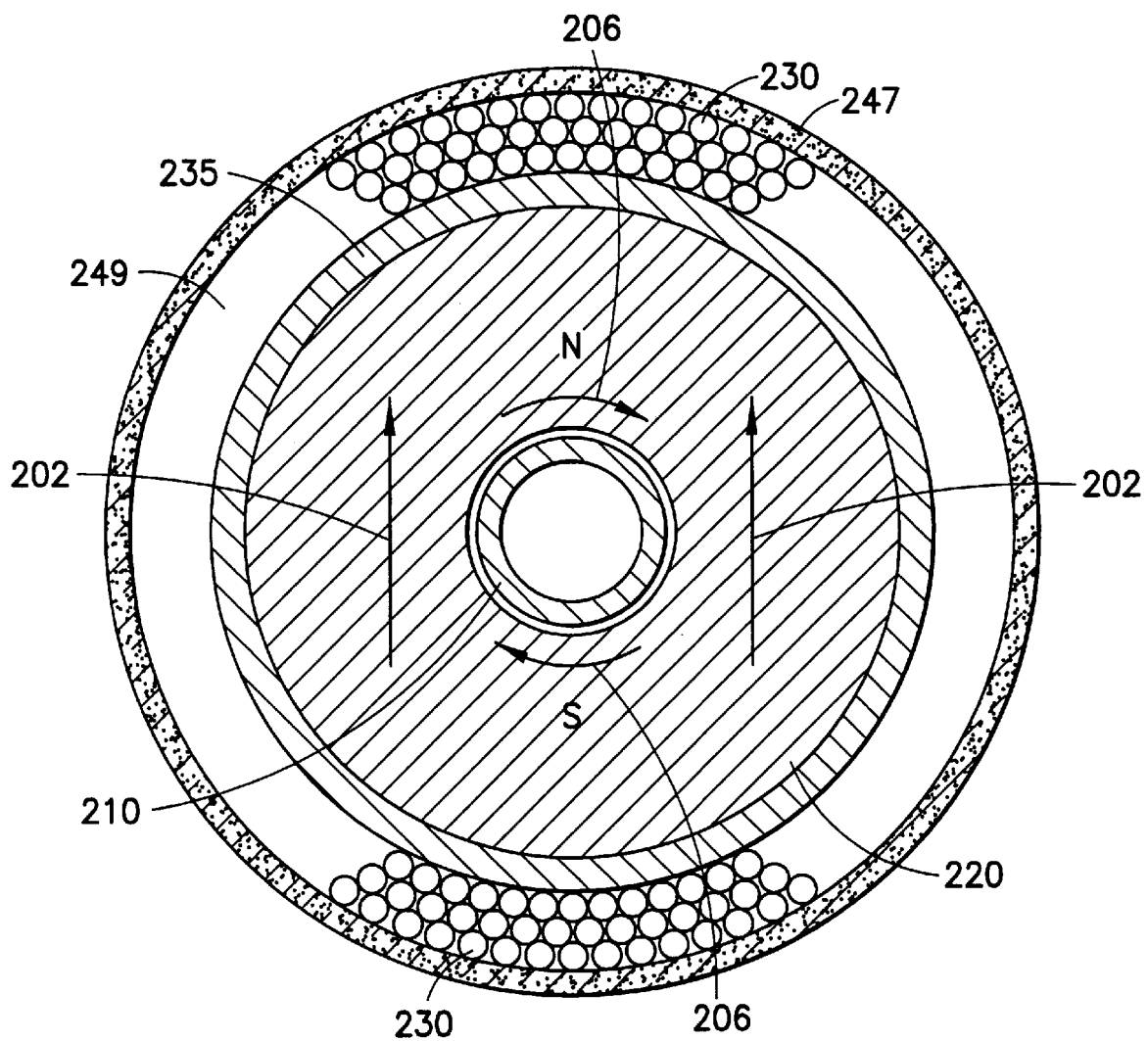
FIG. 2 is a diagram of a cross-section of an embodiment of a logging device that can be used in practicing embodiments of the invention.

FIG. 2 shows a cross-sectional view of an embodiment of the logging device 30 of FIG. 1. A hollow central cylindrical shaft 210 can carry the wiring, and has a generally cylindrical magnet 220 rotatably mounted thereon. The rotation is represented by arrows 206. The magnet is elongated along the longitudinal axis of the device (see FIG. 3), which generally corresponds with the longitudinal axis of the borehole, and is perpendicular to the plane of the paper in FIG. 2. The magnet 220 can be, for example, a ceramic magnet that is polarized, for example, as shown in FIG. 2; that is, transverse (arrows 202) the direction of the longitudinal axis, so that opposite poles (e.g. "N" and "S" in the Figure) are on opposing sides of the cylinder. This produces a static magnetic field having a pattern of magnetic field lines extending generally radially from the poles and then azimuthally in the formations, as in a dipole pattern. The axial extent of the magnetic field pattern will depend on the axial extent of the magnet. A coil 230, which in this embodiment is a multi-turn coil, is wound on a generally cylindrical coil form 235, and has an axis that is perpendicular to the longitudinal axis of the logging device. A cylindrically shaped protective fiberglass housing 247 covers the coil 230, and pressure compensated oil can be provided in the annulus 249. When an AC energizing signal is applied to the coil, this will produce a time varying magnetic field in the formation that is generally of similar shape (although of different orientation for the particular positions of coil and magnet shown in FIG. 2) to that produced by the permanent magnet 220; that is, in this case, a magnetic field that extends radially from the coil axis into the formations and then has an azimuthal orientation in the formations and returns radially back into the coil along the coil axis. The coil 230 is preferably elongated in the longitudinal direction (see FIG. 3), and the vertical extent of the time varying magnetic field will depend on the vertical extent of the coil.

Figure 3:
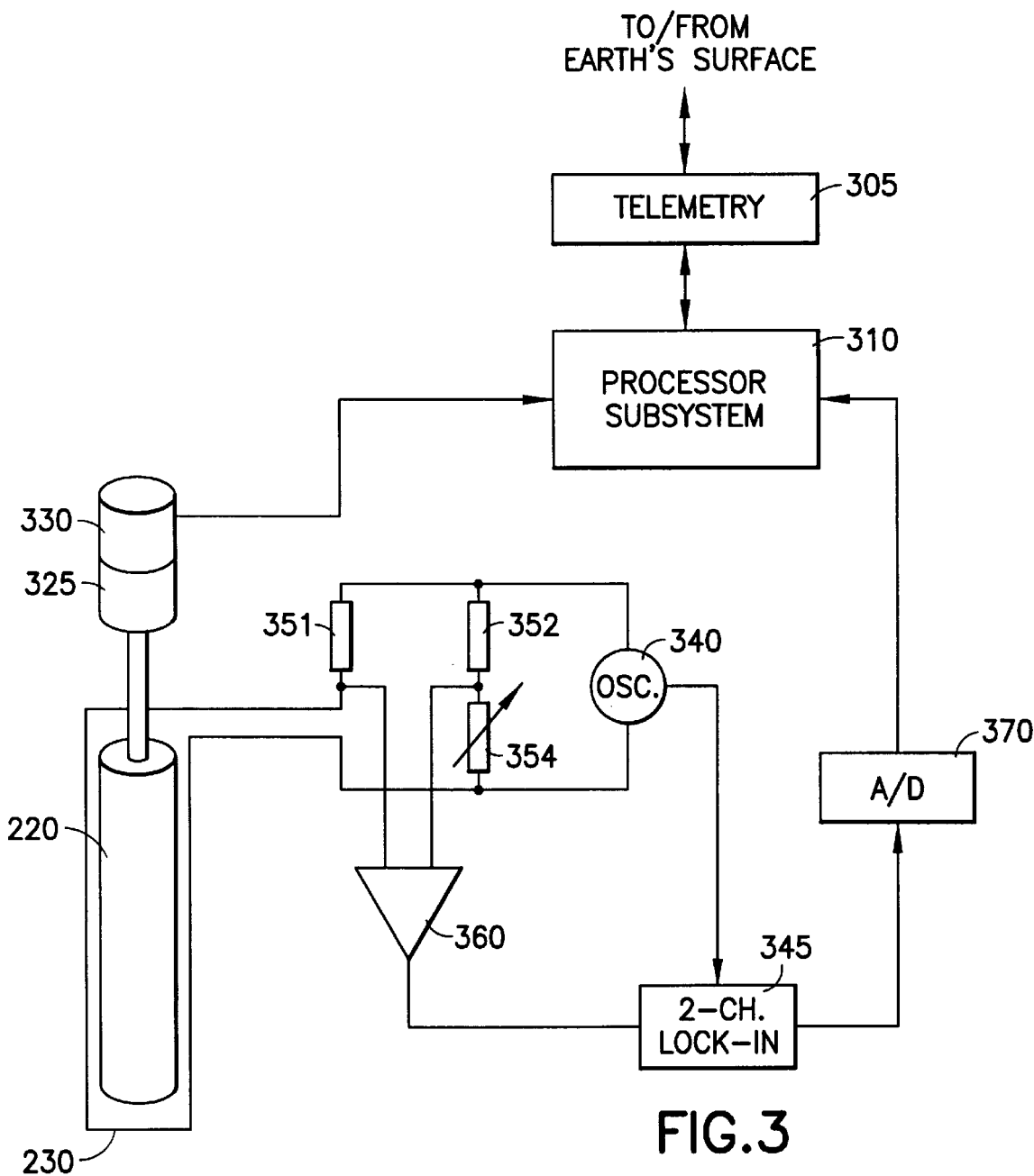
FIG. 3 is a block diagram of downhole circuitry that can be used in practicing embodiments of the invention.

FIG. 3 shows a block diagram, partially in schematic form, of an embodiment of circuitry used in conjunction with the logging device 30 of FIG. 2. In the FIG. 3 diagram, a downhole processor subsystem is represented at 310. The processor subsystem 310 has associated memory, timing, interfaces, and peripherals (not separately shown), as is well known in the art. The processor subsystem 310 is conventionally coupled with telemetry circuitry 305 for communication with the earth's surface. The magnet 220 is mechanically coupled to a motor 325 and a position encoder 330, which is, in turn, electronically coupled with processor subsystem 310. The coil 230 (one turn of which is shown in FIG. 3) is coupled with an audio frequency (AF) oscillator 340, an output of which is also coupled, as a reference signal, to a two-channel lock-in circuit 345. Coupled between oscillator 340 and coil 230 is a bridge circuit 350, whose output is coupled, via amplifier 360, to the other input of the two channel lock-in circuit 345. The bridge circuit 350 includes resistors 351 and 352, and variable resistor 354 that is used for tuning the bridge. The output of the two channel lock-in circuit 345 is coupled to an analog-to-digital converter 370, the output of which is coupled to the processor subsystem 310.

In operation, the spins in the formation are tipped by adiabatic fast passage. [See, for example, A. Abragam, The Principles Of Nuclear Magnetism, Oxford University Press 1961.] The AF oscillator frequency is kept constant at the Larmor frequency for earth's magnetic field in the region being logged. Rotating the permanent magnet 220 by one turn sweeps the magnitude of the total static field twice through the magnitude of the geomagnetic field. Each adiabatic fast passage nutates the spins by 180°. This technique does not produce spin echoes. The precessing transverse nuclear magnetization is detected during the adiabatic fast passage, by observing small changes in the impedance of coil 230 that are coherent with the rotation of the magnet 220. Fast passages are repeated in quick succession. This provides information about the T1 of the formation fluids. If T1 is much shorter than the time duration between consecutive back-and-forth adiabatic passages, then the signal in the two passages are of the opposite sign. Conversely, if T1 is longer than the time duration between consecutive back-and-forth adiabatic passages, then the signal in the two passages are of the same sign.

The magnet 220 raises the magnetic field in the borehole far above the geomagnetic field. Therefore, the borehole is not resonant and there is no need to dope the mud.

Figure 4A:
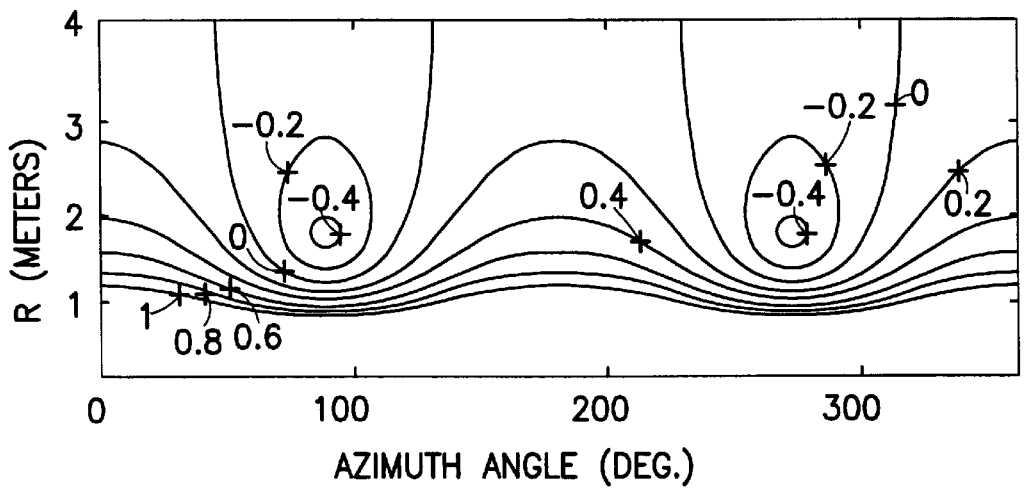
FIG. 4A, FIG. 4B and FIG. 4C, are contours of iso-intensity of the total static field around the logging device. The angular position of the permanent magnet is incremented by 90 degrees in the three plots. The horizontal and vertical axes indicate position around the tool in cylindrical coordinates.
Figure 4B:
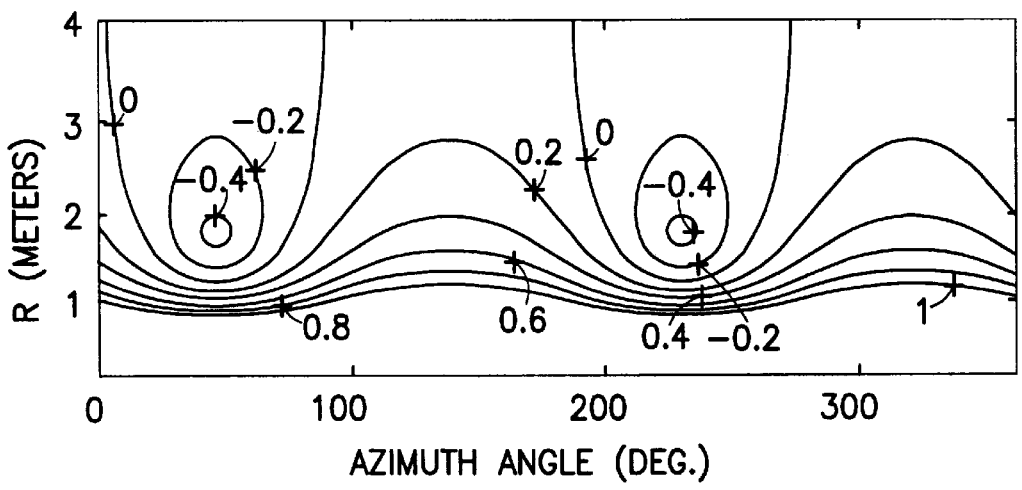
Figure 4C:
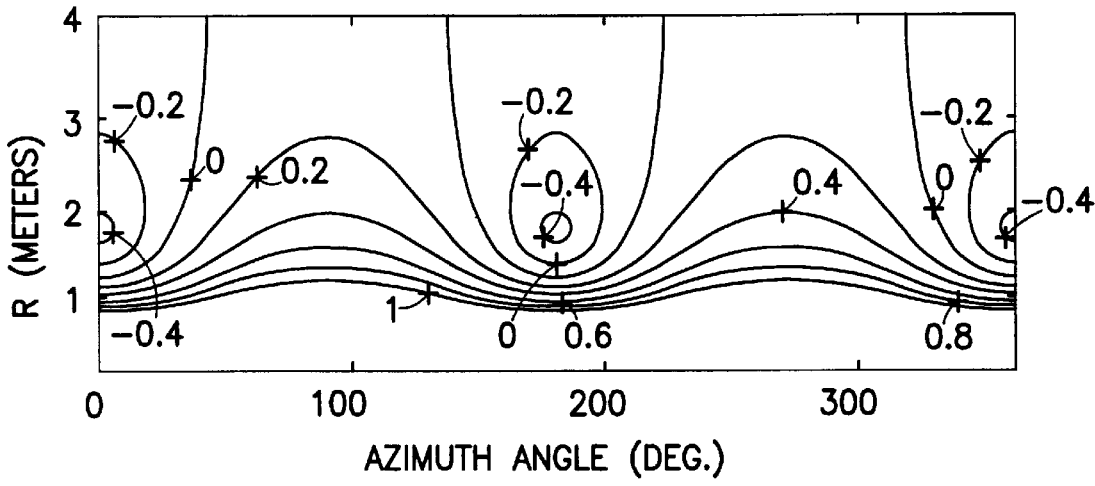

Contours of iso-intensity of the total static magnetic field around the logging tool are shown in FIGS. 4A, 4B, and 4C. The contours are anotated by the deviation from the geomagnetic field intensity, in Gauss. The thick contour indicates where the magnitude of the total field is equal to the unperturbed geomagnetic field. This is where adiabatic fast passage is taking place. This contour rotates in lock-step with the magnet, leaving behind a volume of inverted spins. No fast passage occurs at points closer to the tool than a particular distance that depends on the geometry and strength of the magnet. For example, if the magnet is arbitrarily long, the ceramic magnet has a 0.4 T remnant field, and its inner and outer radii are 7.5 and 8.0 cm, respectively, the particular distance would be about one meter.

In operation of the circuit of FIG. 3, the impedance of coil 230 is measured by tuning the bridge to minimize its output. In one mode of operation, the bridge is nulled (under control of processor subsystem 310) with a time constant that is slow compared to the rotation of the magnet 220. Small fluctuations at the output of the bridge are measured by the lock-in circuit 345, converted to digital form (by A/D convertor 370) and recorded by processor subsystem 310.

The disclosed embodiment of the invention works best if the geomagnetic field is perpendicular to the axis of the logging tool. The invention will not work in situations where the tool axis and the geomagnetic field are parallel. Operation of the tool and the interpretation of the results requires the knowledge of the magnitude of the geomagnetic field, and the angle between the geomagnetic field and the tool axis. The azimuth angle of the geomagnetic field with respect to the tool axis is irrelevant.

What is claimed is:

1. Apparatus for measuring a nuclear magnetic resonance characteristic of earth formations surrounding a borehole, comprising:

a logging device movable through the borehole;

means, in said logging device, for producing a static magnetic field in formations surrounding the borehole;

means, in said logging device, for producing an audio frequency magnetic field in said formations;

means, in said logging device, for rotating said static magnetic field with respect to said audio frequency magnetic field; and means, in said logging device, for detecting nuclear magnetic resonance signals from spins in the formations precessing around earth's magnetic field.

2. Apparatus as defined by claim 1, wherein said means for rotating said static magnetic field with respect to said audio frequency magnetic field comprises means for mechanically rotating said static magnetic field producing means.

3. Apparatus as defined by claim 1, wherein said means for producing a static field comprises a permanent magnet.

4. Apparatus as defined by claim 2, wherein said means for producing a static field comprises a permanent magnet.

5. Apparatus as defined by claim 3, wherein said logging device has a longitudinal axis, and wherein said permanent magnet is elongated in the direction of said longitudinal axis, and wherein said magnet is polarized in a direction transverse the direction of said longitudinal axis.

6. Apparatus as defined by claim 4, wherein said logging device has a longitudinal axis, and wherein said permanent magnet is elongated in the direction of said longitudinal axis, and wherein said magnet is polarized in a direction transverse the direction of said longitudinal axis.

7. Apparatus as defined by claim 3, wherein said audio frequency is a frequency in the range between about 1 kHz to 3 kHz.

8. Apparatus as defined by claim 6, wherein said audio frequency is a frequency in the range between about 1 kHz to 3 kHz.

9. Apparatus as defined by claim 1, wherein said means for producing said audio frequency magnetic field comprises a coil and means for applying an audio frequency energizing signal to said coil.

10. Apparatus as defined by claim 3, wherein said means for producing said audio frequency magnetic field comprises a coil and means for applying an audio frequency energizing signal to said coil.

11. Apparatus as defined by claim 6, wherein said means for producing said audio frequency magnetic field comprises a coil and means for applying an audio frequency energizing signal to said coil.

12. Apparatus as defined by claim 9, wherein said logging device has a longitudinal axis, and wherein said coil is wound on an axis that is perpendicular to said longitudinal axis.

13. Apparatus as defined by claim 10, wherein said logging device has a longitudinal axis, and wherein said coil is wound on an axis that is perpendicular to said longitudinal axis.

14. Apparatus as defined by claim 12, wherein said coil is elongated in the direction of the longitudinal axis.

15. Apparatus as defined by claim 13, wherein said coil is elongated in the direction of the longitudinal axis.

16. Apparatus as defined by claim 9, wherein said means for detecting nuclear magnetic resonance signals from spins precessing around earth's magnetic field comprises means for detecting impedance changes in said coil.

17. Apparatus as defined by claim 13, wherein said means for detecting nuclear magnetic resonance signals from spins precessing around earth's magnetic field comprises means for detecting impedance changes in said coil.

18. Apparatus as defined by claim 17, wherein said means for detecting impedance changes in said coil is operative to detect impedance changes that are coherent with the rotation of said magnet.

19. A method for measuring a nuclear magnetic resonance characteristic of earth formations surrounding a borehole, comprising the steps of:

providing a logging device that is movable through the borehole;

producing, from said logging device, a static magnetic field in formations surrounding the borehole;

producing, from said logging device, an audio frequency magnetic field in said formations;

rotating said static magnetic field with respect to said audio frequency magnetic field; and detecting, at said logging device, nuclear magnetic resonance signals from spins in the formations precessing around earth's magnetic field.

20. The method as defined by claim 19, wherein said step of rotating said static magnetic field with respect to said audio frequency magnetic field comprising mechanically rotating said static magnetic field producing means.

21. The method as defined by claim 20, wherein said step of producing a static field comprises providing a permanent magnet.

22. The method as defined by claim 19, wherein said audio frequency is a frequency in the range between about 1 kHz to 3 kHz.

23. The method as defined by claim 19, wherein said step of producing said audio frequency magnetic field comprises providing a coil and applying an audio frequency energizing signal to said coil.

24. The method as defined by claim 22, wherein said step of producing said audio frequency magnetic field comprises providing a coil and applying an audio frequency energizing signal to said coil.

25. The method as defined by claim 23, wherein said step of detecting nuclear magnetic resonance signals from spins precessing around earth's magnetic field comprises detecting impedance changes in said coil.

26. Apparatus as defined by claim 25, wherein said step of detecting impedance changes in said coil includes detecting impedance changes that are coherent with the rotation of said magnet.

* * * * *